(12) United States Patent
Nair et al.

(10) Patent No.: US 7,195,784 B2
(45) Date of Patent: Mar. 27, 2007

(54) CYCLOOXYGENASE-2 INHIBITORY WITHANOLIDE COMPOSITIONS AND METHOD

(75) Inventors: Muraleedharan G. Nair, Okemos, MI (US); Bolleddula Jayaprakasam, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1007 days.

(21) Appl. No.: 10/294,106

(22) Filed: Nov. 14, 2002

(65) Prior Publication Data

US 2004/0096524 A1    May 20, 2004

(51) Int. Cl.
*A01N 65/00* (2006.01)

(52) U.S. Cl. .................................... 424/725
(58) Field of Classification Search ................ 424/725
See application file for complete search history.

(56) References Cited

U.S. PATENT DOCUMENTS 5,494,668 A * 2/1996 Patwardhan
5,683,698 A * 11/1997 Chavali et al.

FOREIGN PATENT DOCUMENTS

| JP | 410036216 | * | 2/1998 |
| JP | 410036216 A | * | 2/1998 |
| JP | 0200105895 | * | 3/2001 |
| JP | 2002145794 | * | 5/2002 |
| WO | WO 200067768 | * | 11/2000 |
| ZA | 9500908 | * | 12/1995 |

OTHER PUBLICATIONS

Printout showing Jp 2001058951 same as US Paten 6514538.*
Printout showing WO 200067768 is the same as US Patent 6866872.*
Thakur, R.S., et al., Major Medicinal plants of India; Ed.; Central Institute of Medicinal and Aromatic Plants: Lucknow, India, 531 (1989).
Ray, A.B., et al., Prog. Chem. Org. Nat. Prod. 63, 1-106 (1994).
Matsuda, M., et al., Bioorg. Med. Chem. 9, 1499-1507 (2001).
Stoller, E.W., et al., Lloydia, 37, 309,312 (1974).
Monika, P., et al., Asian J. Chem. 6, 442-444 (1994).
Monika, P., et al., Wsci. Phys. Sci. 5, 81-83 (1993).
Misico, R.I., et al., J. Nat. Prod. 65, 677-680 (2002).
Su, B.N., et al., Tetrahedron 58, 3453-3466 (2002).
Smith, W. L., et al., Anu. Rev. Biochem. 69:145-182 (2000).
Patti, R., et al., Cancer Lett. 180:13-21 (2002).
Ohno, R., et al., Cancer 91:1876-1881 (2001.
Khuder, S.A., et al., British Journal of Cancer 84:1188-1192 (2001).
Atta-ur-Rahman; Jamal, S.A.; Choudhary, M.I. Heterocycles 34:689-698 (1992).
Anjaneyulu, A.S.R., et al., Indian J. Chem. Sect.B 36:161-165 (1997).
Pelletier, S.W., et al., Heterocycles 15:317-320 (1981).
Kirson, I., et al., Tetrahedron 26:2209-2219 (1970).
Ghosal, B., et al., Ind. J. Nat. Prod. 4:12-13 (1988).
Shingu, K., et al., Chem. Pharm. Bull. 40:2088-2091 (1992).
Wang, H., et al., J. Nat. Prod. 62:294-296 (1999).
Ramsewak, R.S., et al., Phytomedicine 7:303-308 (2000).

* cited by examiner

*Primary Examiner*—Michael Meller
(74) *Attorney, Agent, or Firm*—Ian C. McLeod; Steven E. Merritt

(57) ABSTRACT

Cyclooxygenase-2 enzyme inhibiting withanolides are described. In particular, compounds from *Withania somnifera* are the preferred source of the withanolides, although they can be from other plant sources. The COX-2 inhibition is selective over COX-1.

4 Claims, 7 Drawing Sheets

| | R | R' |
|---|---|---|
| 1 | Glc-(1→6)-Glc-(1→4)-Glc | H |
| 2 | Glc | Glc |
| 11 | Glc | H |
| 12 | Glc-(1→6)-Glc | H |

| | R | R' | R" | R''' |
|---|---|---|---|---|
| 3 | =O | H | H | Glc |
| 4 | -OH | Glc | OH | H |
| 8 | =O | H | H | H |

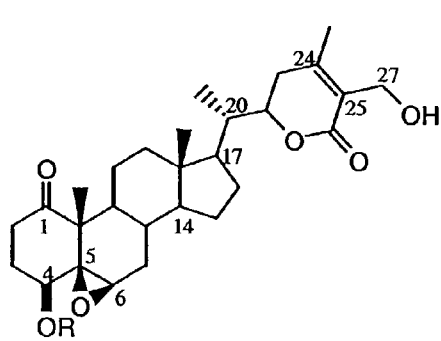
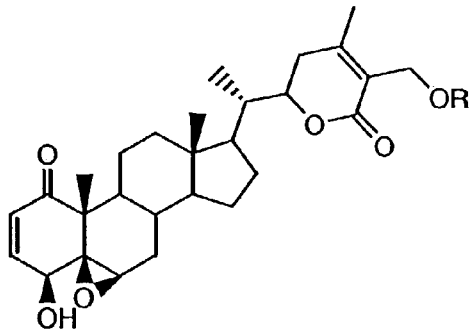
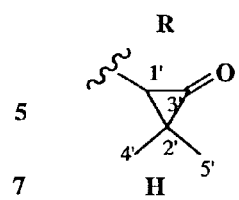
FIGURE 1B
| | R |
|---|---|
| 6 | H |
| 10 | Glc |
FIGURE 1C
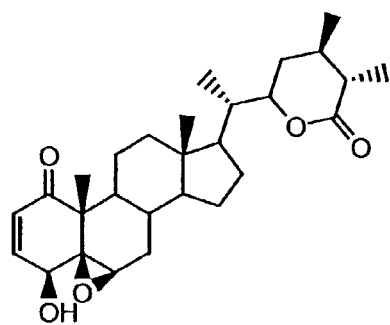
9
FIGURE 1D

CYCLOOXYGENASE-2 INHIBITORY WITHANOLIDE COMPOSITIONS AND METHOD

BACKGROUND OF THE INVENTION

1. Field of the Invention

The present invention relates to the use of withanolides as selective cyclooxygenase-2 (COX-2) inhibitors. The withanolides have little effect on COX-1.

2. Description of Related Art

*Withania somnifera* (L) Dunal of solanaceae, is an erect evergreen shrub distributed throughout the drier parts of India. *W. somnifera*, known as Aswagandha, is well known for its use in Ayurvedic medicine. The Aswagandha root extract was reported as a folk remedy for adenopathy, arthritis, asthma, hypertension, inflammations, and rheumatism (Thakur, R. S., et al., *Major medicinal plants of India;* Ed.; Central Institute of Medicinal and Aromatic Plants: Lucknow, India, 531 (1989)). The leaves of *W. somnifera* were also used as a cure for several illnesses including tumors, inflammations, conjunctivitis and tuberculosis (Thakur, R. S., et al., *Major medicinal plants of India;* Ed.; Central Institute of Medicinal and Aromatic Plants: Lucknow, India, 531 (1989)). Currently, powdered roots or root extract of this plant are used as a dietary supplement in the United States.

The major chemical constituents reported from *W. somnifera* are called withanolides. These compounds are structurally diverse steroidal compounds with an ergosterol skeleton in which C-22 and C-26 are oxidized to form a $\delta$-lactone; (Ray, A. B., et al., *Prog. Chem. Org. Nat. Prod.* 63, 1–106 (1994)). The chemical investigations of the roots and leaves of *W. somnifera* resulted in the isolation and characterization of several withanolides (Matsuda, M., et al., *Bioorg. Med. Chem.* 9, 1499–1507 (2001)). The fruits of this plant are tiny orange berries and reported to contain saturated and unsaturated fatty acids (Stoller E. W., et al., *Lloydia,* 37, 309–312 (1974); Monika, P., et al., *Asian J. Chem.* 6, 442–444 (1994); and Monika, P., et al., *Wsci. Phys. Sci.* 5, 81–83 (1993)). However, leaves and fruits are not fully investigated for biological activities. The withanolides are classified according to their structural skeleton (Ray, A. B., et al., *Prog. Chem. Org. Nat. Prod.* 63, 1–106 (1994)) and the structural variation is responsible for the wide array of pharmacological activities. Withanolides have been studied for their anti-inflammatory, antitumor, cytotoxic, immunomodulating activities and for the protection against $CCl_4$-induced hepatotoxicity (Ray, A. B., et al., *Prog. Chem. Org. Nat. Prod.* 63, 1–106 (1994); and Anjaneyulu, A. S. R., et al., *Studies in Natural Products Chemistry: Structure and Chemistry* (Part F); Ed. Atta-ur-Rahman, Vol. 20, 135–261 (1998)). They were also reported to induce phase-II enzymes in animal models, which is considered to be one of the mechanisms in cancer chemoprevention (Misico, R. I., et al., *J. Nat. Prod.* 65,677–680 (2002); and Su, B. N., et al., *Tetrahedron* 58, 3453–3466 (2002)).

Cyclooxygenase-1(COX-1) and -2(COX-2) enzymes are responsible for the conversion of arachidonic acid, a lipid present in the cell, to prostaglandins. Prostaglandins in turn cause inflammatory responses in the body. Inhibition of COX-1 enzyme may result in the formation of ulcers in many human and hence the selective inhibition of COX-2 enzyme by compounds has a major advantage over non-selective nonsteroidal anti-inflammatory drug (NSAIDs) (Smith, W. L., et al., *Anu. Rev. Biochem.* 69:145–182 (2000)) sold over the counter (OTC). It is important to note that over expression of COX-2 enzyme was observed not only in inflamed cells but also by various types of tumor cells (Patti, R., et al., *Cancer Lett.* 180:13–21 (2002); Ohno, R., et al., *Cancer* 91:1876–1881 (2001); and Khuder, S. A., et al., *British Journal of Cancer* 84:1188–1192 (2001)). Hence, COX-2 inhibitors with little or no COX-1 activity are of great interest for the chemoprevention of cancer.

Objects

It is therefore an object of the present invention to provide compositions and a method for inhibiting COX-2 selectively. It is particularly an object of the present invention to provide a method and compositions which do not inhibit COX-1. These and other objects will become increasingly apparent by reference to the following description and the drawings.

SUMMARY OF INVENTION

The present invention relates to a method for selectively inhibiting COX-2 enzyme relative to COX-1 enzyme which comprises providing an effective amount of a withanolide so as to produce the COX-2 inhibition. Preferably the withanolide is present in plant material of *Withania somnifera*. In particular, the present invention relates to a method for selectively inhibiting COX-2 enzyme relative to COX-1 enzyme which comprises providing an effective amount of an isolated and purified withanolide or mixtures thereof present in *Withania somnifera* so as to produce the COX-2 enzyme inhibition. The inhibition can be in vitro; however, preferably inhibition is in vivo in a mammal.

The method preferably uses a compound selected from the group consisting of physagulin D (1→6)-β-D-glucopyranosyl-(1→4)-β-D-glucopyranoside; 27-O-β-D-glucopyranosyl physagulin D; 27-O-β-D-glucopyranosyl viscosalactone B; 4,16-dihydroxy-5β,6β-epoxyphysagulin D; 4-(1-hydroxy-2,2-dimethylcyclo-propanone)-2,3-dihydrowithaferin A; 2,3-dihydrowithaferin A; viscosalactone B; sitoindoside IX; physagulin D; withanoside IV, withaferin A and mixtures thereof.

Further, the present invention relates to a composition which comprises:

a withanolide or mixtures thereof increased over an amount occurring in nature; and a pharmaceutically acceptable carrier, wherein the composition selectively inhibits COX2 enzyme relative to COX1 enzyme.

Preferably the composition comprises:

an isolated and purified withanolide or mixtures thereof present in *Withania somnifera;* and a pharmaceutically acceptable carrier, wherein the composition selectively inhibits COX2 enzyme relative to COX1 enzyme. In the composition the compound is previously listed.

The present invention also relates to an isolated and purified compound of the formula:

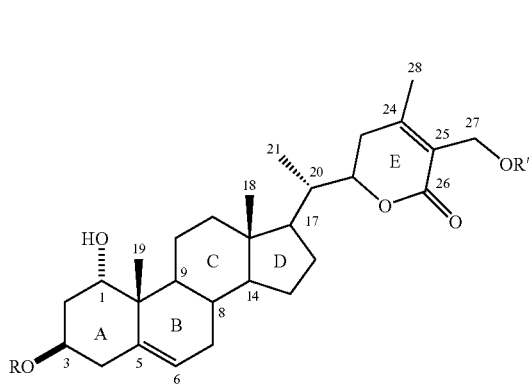

wherein R is Glc-(1→6)-Glc-(1→4)-Glc, where Glc is glucose, and wherein R' is H.

The present invention also relates to an isolated and purified compound of the formula:

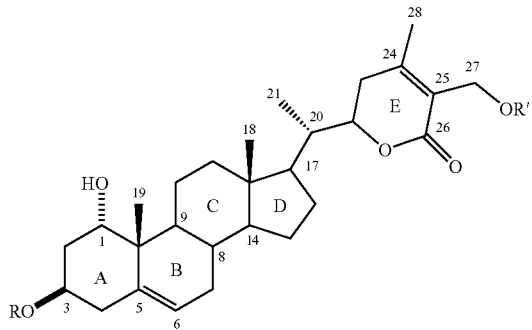

wherein R is Glc and R' is Glc, wherein Glc is glucose.

The present invention also relates to an isolated and purified compound of the formula:

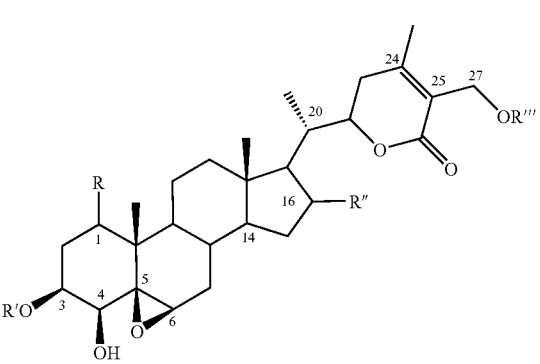

wherein R=O, R'=H, R"=H and R'''=Glc, wherein Glc is glucose.

The present invention relates to an isolated and purified compound of the formula:

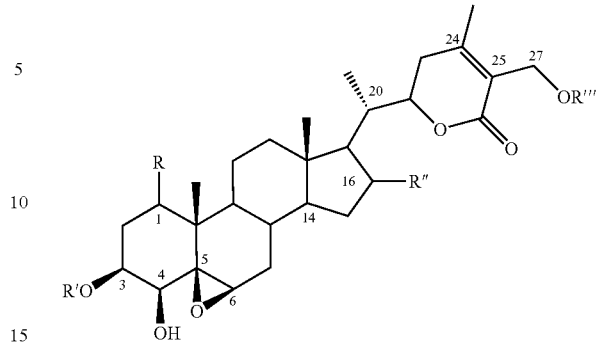

wherein R=—OH, R'=Glc, R'=OH and R'''=H.

Finally, the present invention relates to a purified compound of the formula:

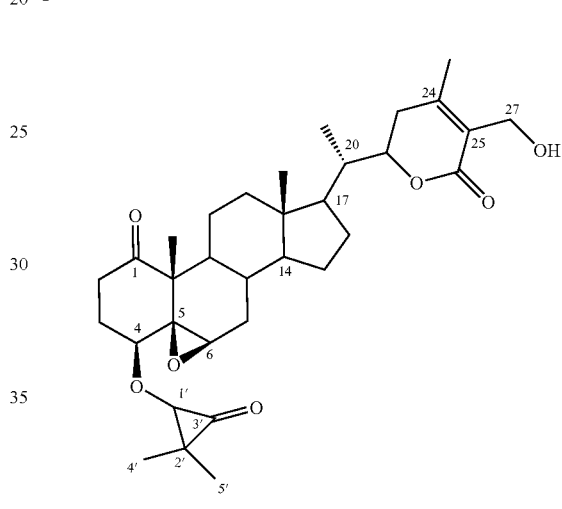

DESCRIPTION OF PREFERRED EMBODIMENTS

It has been discovered that leaf extracts of *W. somnifera* possess excellent selective COX-2 inhibitory activity. The isolation and characterization of several novel withanolides and a number of known withanolides from *W. somnifera* leaf extracts is disclosed. The inhibitory effects of withanolides isolated from the leaves on cyclooxygenase enzymes and their antioxidant activities are also disclosed.

Four novel withanolide glycosides and a withanolide (herein all referred to as "withanolide") have been isolated from the leaves of *Withania somnifera*. The structures of the novel compounds were elucidated as physagulin D (1→6)-β-D-glucopyranosyl-(1→4)-β-D-glucopyranoside (1), 27-O-β-D-glucopyranosyl physagulin D (2), 27-O-β-D-glucopyranosyl viscosalactone B (3), 4,16-dihydroxy-5β,6β-epoxyphysagulin D (4), and 4-(1-hydroxy-2,2-dimethylcyclo-propanone)-2,3-dihydrowithaferin A (5) on the basis of 1D-, 2D-NMR and MS spectral data. In addition, seven known withanolides withaferin A (6), 2,3-dihydrowithaferin A (7), viscosalactone B (8), 23,24-dihydrowithaferin A (9), sitoindoside IX (10), physagulin D (11), and withanolide IV (12) were isolated. These withanolides were assayed to determine their ability to inhibit cyclooxygenase-1 (COX-1) and cyclooxygenase-2 (COX-2) enzymes and lipid peroxidation. The withanolides tested, except compound 9, showed selective COX-2 enzyme inhibition ranging from 9–40% at 100 μg/ml. Compounds 4, 10 and 11 also inhibited lipid peroxidation by 40, 44 and 55%, respectively.

EXAMPLES 1 TO 12

The *W. somnifera* leaf extract purchased was identical to the methanol extract of fresh leaves harvested from *W. somnifera* plants grown in the greenhouses of Bioactive Natural Products and Phytoceuticals laboratory at Michigan State University. The extract was purified by preparative TLC and by HPLC to yield pure withanolides 1–12.

Compound 1 was isolated as an amorphous powder and its molecular formula was determined as $C_{46}H_{73}O_{20}$ by HRFABMS as indicated by an $[M+H]^+$ ion at m/z 945.4682 (calc. 945.4695). Compound 1 showed absorption bands in its IR spectrum at 3406 and 1698 cm$^{-1}$, respectively, corresponding to an –OH and an α,β-unsaturated lactone moieties. Three anomeric protons doublets at δ 4.22, 4.20 and 4.15 were correlated to three anomeric carbons at δ 103.0, 103.9 and 104.8, respectively, in its HMQC spectrum and suggested that compound 1 contained a triglycosidic moiety. Apart from the glycosidic signals, compound 1 exhibited signals for 28 carbons. The signals at 80.1, 32.8, 160.4, 123.6, and 168.6 ppm were assigned to a six-membered ring α,β-unsaturated δ-lactone moiety in the molecule and the olefinic carbons at δ 139.0 and 125.5 were assigned to C-5 and C-6. The DEPT spectrum of compound 1 showed the presence of three methine carbons at δ 74.9, 73.6, 80.1 and a methylene carbon at δ 57.6 and were indicative of C-1, C-3, C-22 and C-27 oxygenated carbons.

Figure 1:
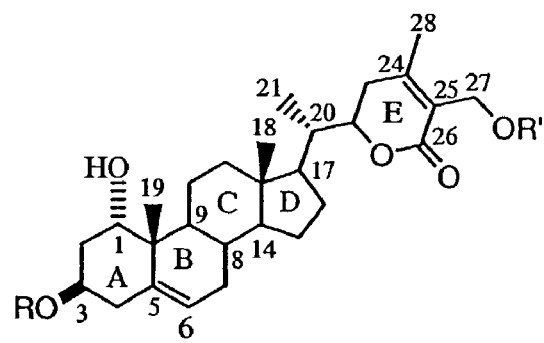
FIGS. 1 to 1D are chemical formulas showing the structures of withanolides 1 to 12.
Figure 1A:
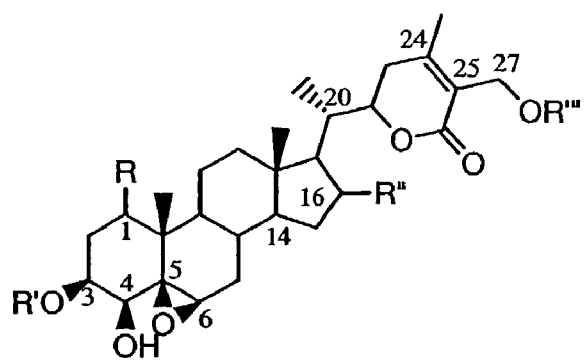
Figure 2A:
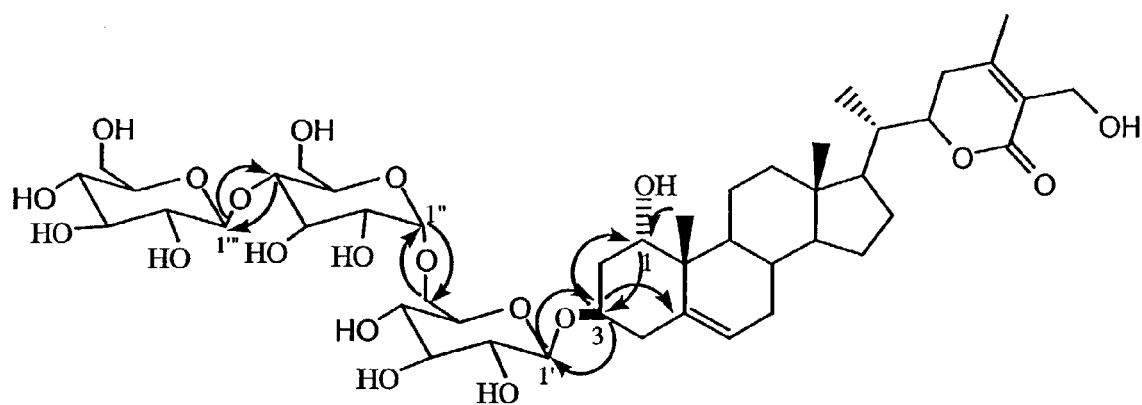
FIGS. 2A to 2E are chemical formulas showing some of the significant HMBC (→) correlations observed in compounds 1,2,3,4 and 5.

The singlets at δ 0.60, 0.90, and 1.90 and a doublet at 0.92 ppm in its $^1$H NMR were assigned to C-18, 19, 28 and 21, respectively. An olefinic proton at δ 5.50 was placed at C-6 as it showed correlations with this carbon at 125.5 ppm in its HMQC. The C-6' and C-4" of the sugar units in compound 1 appeared at 70 and 77.8 ppm, respectively. These carbons normally appear at around 62 and 71 ppm, respectively, in glucose that are not conjugated. The attachment of one of the glucose units to C-3 of the aglycone was confirmed by the HMBC correlations (FIG. 2A) observed between H-1' and δ 4.22 and C-3 at 73.6 ppm. Other HMBC correlations significant to glucose linkages in compound 1 (FIG. 2A) were H-1" at δ 4.20 to C-6' at δ 70.0 and H-1'" at δ 4.15 to C-4" at 77.8 ppm, respectively. Acid hydrolysis of compound 1 gave only D-glucose and the aglycone. The $^1$H-NMR spectral data of the aglycone was identical to the published spectral data of sominone (Atta-ur-Rahman; Jamal, S. A.,; Choudhary, M. I. *Heterocycles* 34:689–698 (1992)). Also, the $^{13}$C NMR data of compound 1 was compared to sominone, obtained as a hydrolysis product of physagulin D (11) in our laboratory. Therefore, glucose linkages in compound 1 were established as [β-D-glucopyranosyl-(1→6)-β-D-glucopyranosyl-(→4)β-D-glucopyranoside]. The mass spectral fragments obtained at m/z 783, 621 and 459 for compound 1 in its FABMS showed the successive loss of three glucose units which further confirmed the proposed structure of compound 1 as Physagulin D (1→6)-β-D-glucopyranosyl-(1→4)-β-D-glucopyranoside.

Figure 2B:
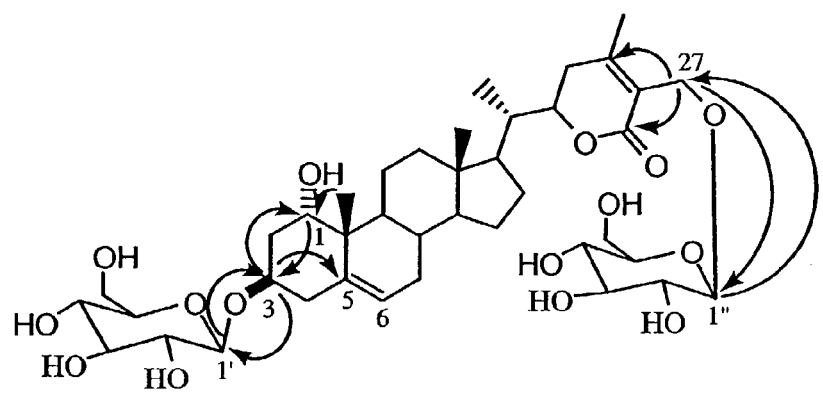

The IR spectrum of Compound 2, isolated as an amorphous powder, showed absorption bands at 3407, 1696 cm$^{-1}$ were due to the hydroxyl and an α,β-unsaturated δ-lactone carbonyl functionalities. The mass spectrum of 2 displayed an $[M+H]^+$ ion at m/z 783.4168 (calc. 783.4188), which was consistent with the molecular formula as $C_{40}H_{63}O_{15}$. The $^1$H NMR signals appeared as singlets at δ 0.76, 1.01 and 2.11, respectively, were assigned to three methyl groups in 2. It also showed one methyl doublet at δ 1.22, C-27 methylene protons as doublets, integrated for one proton each, at δ 4.60 and 4.46, two oxymethine multiplets at δ 4.50 and 3.83 and an olefinic proton at δ 5.49. $^{13}$C NMR of 2 exhibited signals for an α,β-unsaturated δ-lactone carbonyl at δ 168.6, two oxygenated methines at δ 74.9 and 73.6 and olefinic carbons at δ 139.1 and 125.4. The NMR spectra of compound 2 were similar to that of 1, with a major difference due to the absence of one of the sugars as indicated by the lack of anomeric proton and carbon signals at δ 4.20 and 104.8, respectively. Acid hydrolysis of 2 gave D-glucose and sominone (Atta-ur-Rahman, et al., *Heterocycles* 34:689–698 (1992)), identified by comparing the TLC with hydrolysis products of 1. Compound 2 gave a molecular ion at m/z 783, which is 162 amu less than that of 1, suggested that its probable structure was simonene diglucoside. One of the glucose units in compound 2 was assigned at C-3 based on the HMBC correlations (FIG. 2B) observed between H-3 at δ 3.83 and C-1' at δ 102.7. The second glucose unit in compound 2 was assigned at C-27 as this carbon at δ 63.5 was shifted to downfield by 5.9 ppm when compared to the chemical shift of similar carbon in 1 at δ 57.6. The linkage in compound 2 was further supported by its HMBC spectral correlations (FIG. 2B) observed between C-27 at δ 63.5 and H-1" at δ 4.31. The placement of sugar units at C-3 and C-27 was further confirmed by comparison of $^{13}$C NMR data of A-ring and lactone ring carbons in 2 with that of physagulin D (11) and sitoindoside IX (10). Therefore, structure of 2 was concluded as 27-O-β-D-glucopyranosyl physagulin D.

The HRFABMS of Compound 3, obtained as an amorphous powder, revealed an $[M+Na]^+$ peak at m/z 673.3200 (calc. 673.3224) and corresponded to a molecular formula of $C_{34}H_{50}O_{12}$. The IR spectrum of compound 3 indicated the presence of hydroxyl, α,β-unsaturated δ-lactone and a six-membered ring ketone in the molecule as indicated by absorption bands at 3425, 1700, 1652 cm$^{-1}$, respectively. The $^1$H NMR spectrum of compound 3 displayed signals for three oxygenated methine protons at δ 3.66, 3.33 and 4.44, four methyls at δ 0.67, 0.98, 1.18, and 2.1 and oxymethylene protons at δ 4.59 and 4.45. It also showed a doublet for an anomeric proton at δ 4.31 and a broad singlet at 3.15 ppm, which correlated to the anomeric carbon at δ 102.7 and an epoxide carbon at δ 56.6 in its HMQC, respectively. The $^{13}$C NMR spectrum showed signals due to carbonyl carbon of a keto group at δ 210.2; an epoxide moiety at δ 63.8 and 56.6 and for a six-membered ring α,β-unsaturated lactone moiety at δ 78.9, 29.6, 159.1, 122.5 and 167.4. The spectral data suggested that compound 3 was closely related to viscosalactone B (8).

Figure 2C:
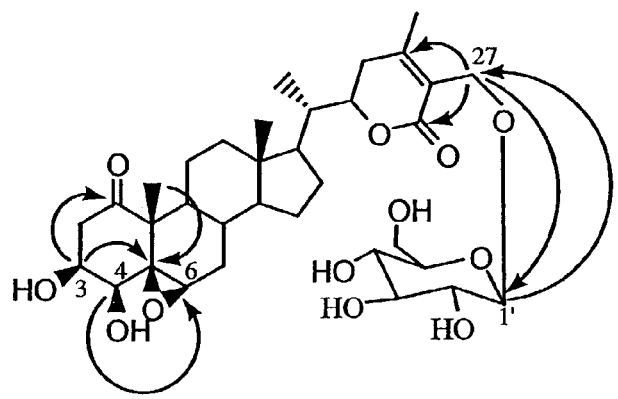

Hydrolysis of compound 3 gave viscosalactone B (8) and D-glucose as confirmed by spectral studies. This indicated that compound 3 was a viscosalactone glucoside. Analyses of its HMBC spectrum (FIG. 2C) suggested that the glucose moiety was attached to C-27 as this carbon at δ 61.6 correlated with the anomeric proton at 4.31 ppm. Linkage of one of the glucose units to C-27 was also supported by the downfield shift of C-27 by 5.3 ppm as compared to its aglycone viscosalactone B (9), which appeared at δ 57.1. The spectral evidence confirmed the structure of compound 3 as 27-O-β-D-glucopyranosyl viscosalactone B (3).

Compound 4 was obtained as an inseparable mixture with compound 12 and the ratio was about 2:1. The HRFABMS displayed an [M+H]$^+$ ion at m/z 669.3456 (calc. 669.3486) which corresponded to the molecular formula $C_{34}H_{53}O_{13}$. The base peak at m/z 507, produced by the loss of 162 amu from the molecular ion, indicated that compound 4 contained a mono glycoside. $^1$H- and $^{13}$C NMR assignments for compound 4 were unambiguously assigned by supporting evidences from DEPT, HMQC and HMBC spectral studies.

Figure 2D:
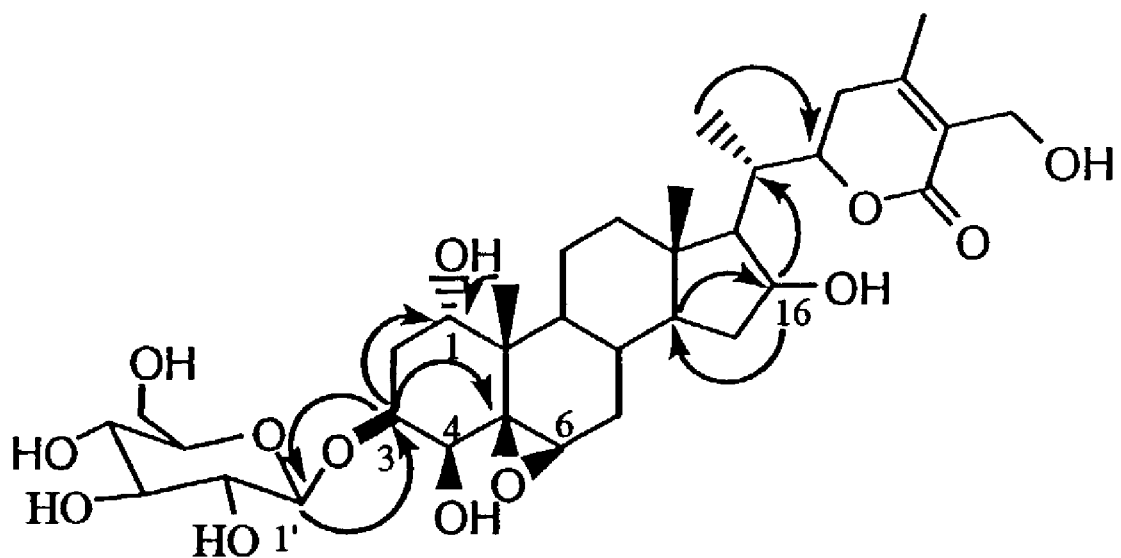

Apart from the sugar carbons, $^{13}$C NMR and DEPT spectra displayed signals for four methyl groups at δ 11.9, 13.6, 15.0 and 20.0, α,β-unsaturated δ-lactone carbonyl at δ 168.5 and oxygenated methines at δ 79.0, 75.6, 73.6, and 59.4. The molecular ion at m/z 669, 48 amu higher than that of physagulin D (m/z 621), indicated that compound 4 contained three additional oxygen functionalities in its structure. One such oxygen functionality, assigned as an epoxide at C-5 and C-6, resonated at δ 65.5 and 59.4, respectively in its $^{13}$C NMR spectrum. The second and third oxygen functionalities were determined as hydroxyl groups and were placed at C-4 and C-16 as confirmed by HMBC experiments (FIG. 2D). Comparison of $^1$H and $^{13}$C NMR data of 4 with physagulin D indicated that the sugar moiety was glucose and it was linked to C-3 of the molecule. The linkage of glucose unit to C-3 was also substantiated by HMBC correlations (FIG. 2D) observed between C-3 at δ' 73.6 and H-1' at δ 4.38. Therefore, the structure of 4 was confirmed as 4,17-dihydroxy-5β,6β-epoxyphysagulin D.

Figure 2E:
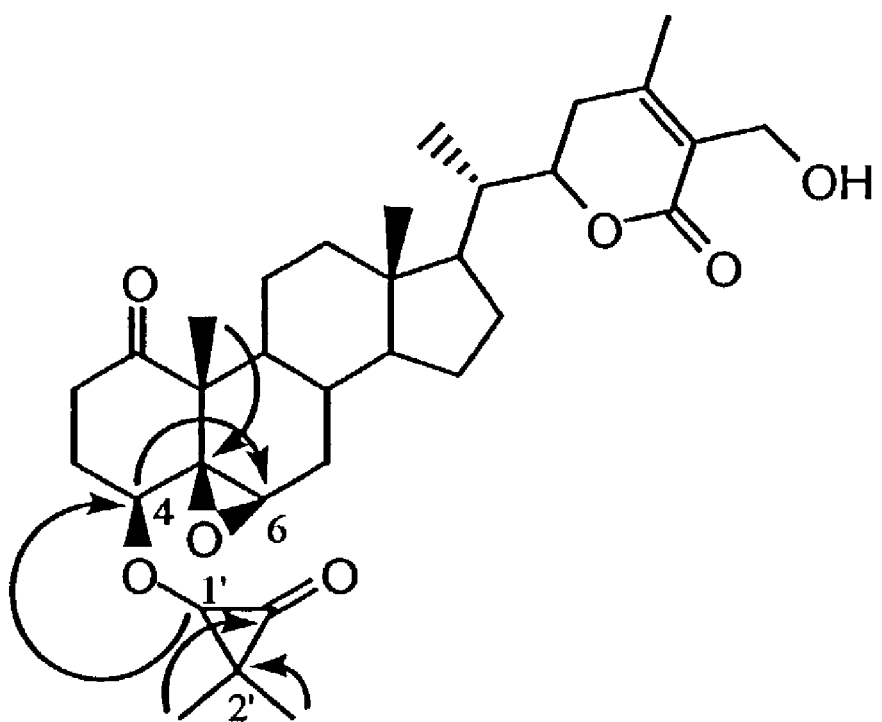

The IR spectrum of compound 5, isolated as an amorphous powder, showed absorption bands for an —OH and a δ-lactone carbonyl group at 3434 cm$^{-1}$ and 1704 cm$^{-1}$, respectively. The HRFABMS gave an [M+H]$^+$ ion at m/z 555.3335, which analyzed for $C_{33}H_{47}O_7$ (calc. 555.3323). The $^{13}$C NMR and DEPT spectra of compound 5 showed the presence of six methyl, nine methylene, nine methine and nine quaternary carbons. The $^1$H NMR spectrum of 5 showed signals for four methyl groups at δ 0.69, 0.98, 1.18, and 2.07. Two doublets at δ 4.35 and 4.28 was assigned to two protons of a methylene at C-27. In addition, the proton signal appeared at δ 3.19 was assigned to H-4. The $^{13}$C NMR spectrum of compound 5 was similar to the spectrum of dihydrowithaferin A (7) except that 5 had additional carbon signals at δ 210.1, 52.1, 72.8, and 25.0. The corresponding proton signals in 5 were at δ 1.35 (6H, s) and 3.70 (1H, s). These additional carbon signals accounted for a 2,2-dimethylcyclopropanone moiety in 5, which was supported by both MS and DEPT spectral data. Analyses of the HMBC spectrum revealed that 2,2-dimethylcyclopropanone moiety in 5 was linked via C-4 hydroxyl in dihydrowithaferin A (7) (FIG. 2E). The fragments at m/z 472 [M+H—$C_5H_7O$]$^+$ and 471 [M+H—$C_5H_8O$]$^+$ in its FABMS also supported the proposed structure for compound 5.

Figure 3A:
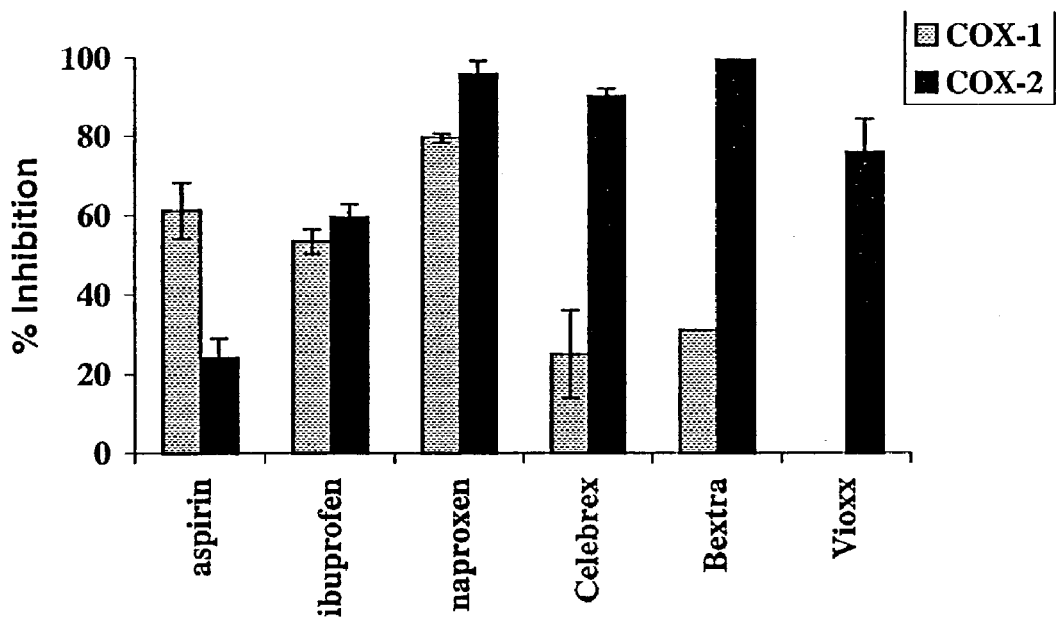
FIG. 3A is a graph showing inhibition of COX-1 and -2 enzymes by commercial non-steroidal anti-inflammatory agents (NSAIDs). Aspirin, ibuprofen and naproxen were tested at 180, 2.1 and 2.5 µg/ml, respectively. Celebrex, Vioxx and Bextra were assayed at 1.67 µg/ml, respectively. DMSO solvent control did not inhibit COX enzymes. Data are represented as mean±one standard deviation (n=2).
Figure 3B:
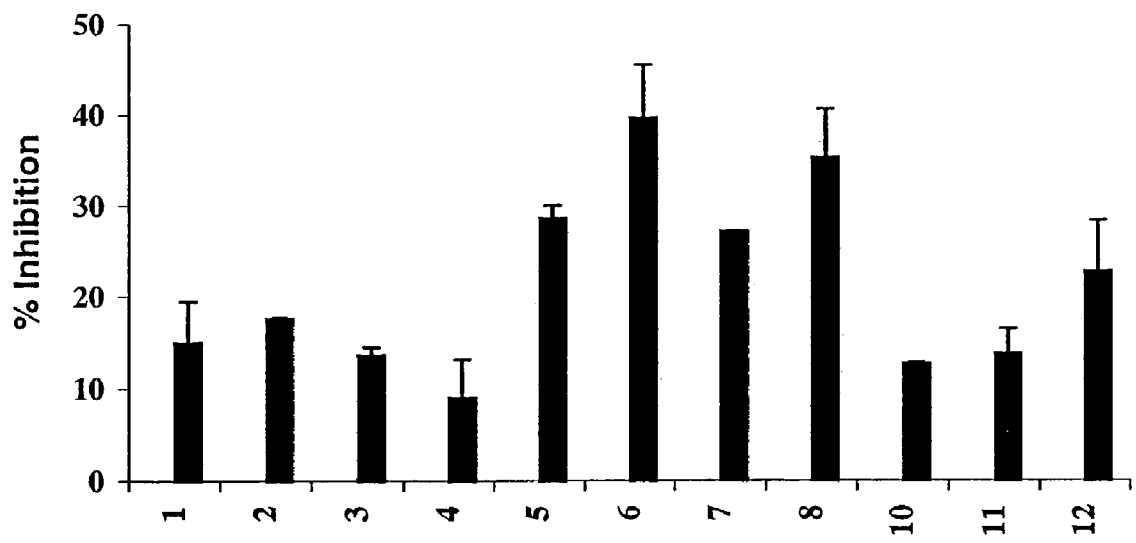
FIG. 3B is a graph showing COX-1 and -2 inhibitory activities of withanolides 1–12 at 100 µg/ml. DMSO solvent control did not inhibit COX enzymes. Vertical bars represent the standard deviation of each data point (n=2). Withanolides 1–12 did not inhibit COX-1 enzyme even at 500 µg/ml concentration.
Figure 4:
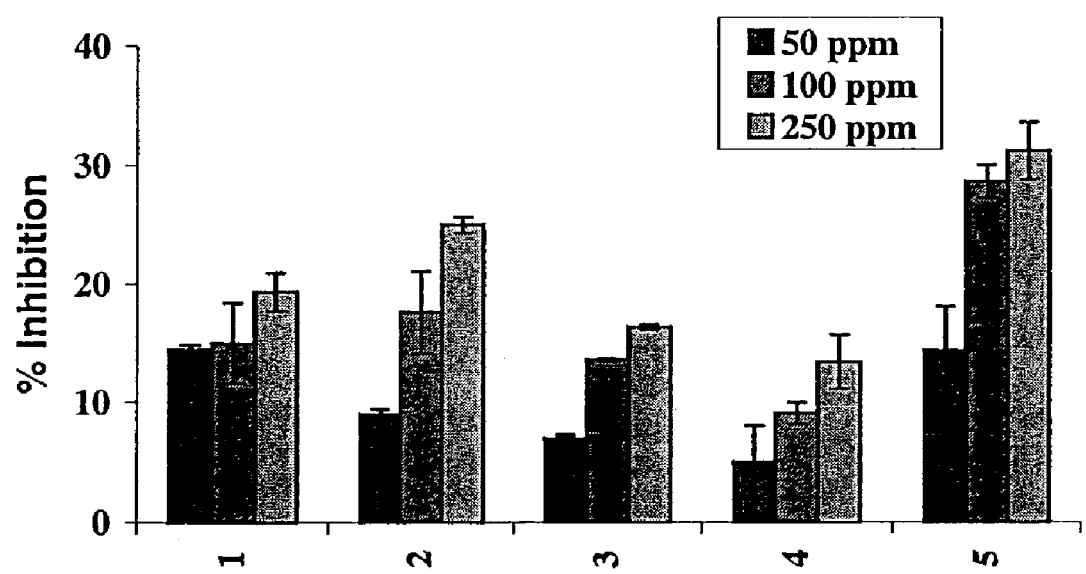
FIGS. 4A and 4B are graphs showing dose dependent inhibition of COX-2 enzyme by compounds 1–5 at 50, 100 and 250 µg/ml. Vertical bars represent the standard deviation of each data point (n=2).

The withanolides isolated from the leaves were evaluated for their cyclooxygenase (COX) enzyme inhibitory activity using prostaglandin endoperoxide synthase isozymes-1 (COX-1) and PGHS-2 (COX-2). Aspirin, ibuprofen, naproxen, Celebrex, and Bextra were used as positive controls and they showed 61, 53, 79, 23 and 25% of COX-1; 7, 59, 95, 98 and 99% of COX-2 inhibition, respectively (FIG. 3A). Vioxx inhibited COX-2 enzyme by 80% and had no COX-1 enzyme inhibition. The novel withanolides 1–5 were tested at 50, 100 and 250 µg/ml and all other withanolides isolated from the leaves were tested at 100 µg/ml concentration. Compounds 6, 7, 8, 10, 11, and 12 gave 39, 27, 35, 13, 14 and 23%, respectively, of COX-2 enzyme inhibition at 100 µg/ml (FIG. 3B). A dose dependent inhibition of COX-2 (FIG. 3) was observed for compounds 1–5 and the activity varied considerably among withanolides at concentrations tested. The COX-2 activity exhibited by compounds 1–5 were 15, 9, 7, 5 and 15%, respectively, at 50 µg/ml (FIG. 4). It is important to note that the withanolides tested did not inhibit COX-1 enzyme even at 500 µg/ml concentration. However, the activity remained the same for all compounds when the concentration was increased from 100 to 250 µg/ml in COX-2 assays. The lack of increased COX-2 activity at higher concentrations is probably due to the solubility of these withanolides under assay conditions. The reduced COX-2 activity of compounds 3 and 10 as compared to 8 and 6 might be due to the glycosylation at C-27 in 3 and 10. Compound 9, which is lacking a double bond between C-23 and C-24, showed neither COX-1 nor COX-2 activities. This indicated that the double bond in α,β-unsaturated δ-lactone moiety is critical for the COX-2 inhibitory activity.

Figure 5:
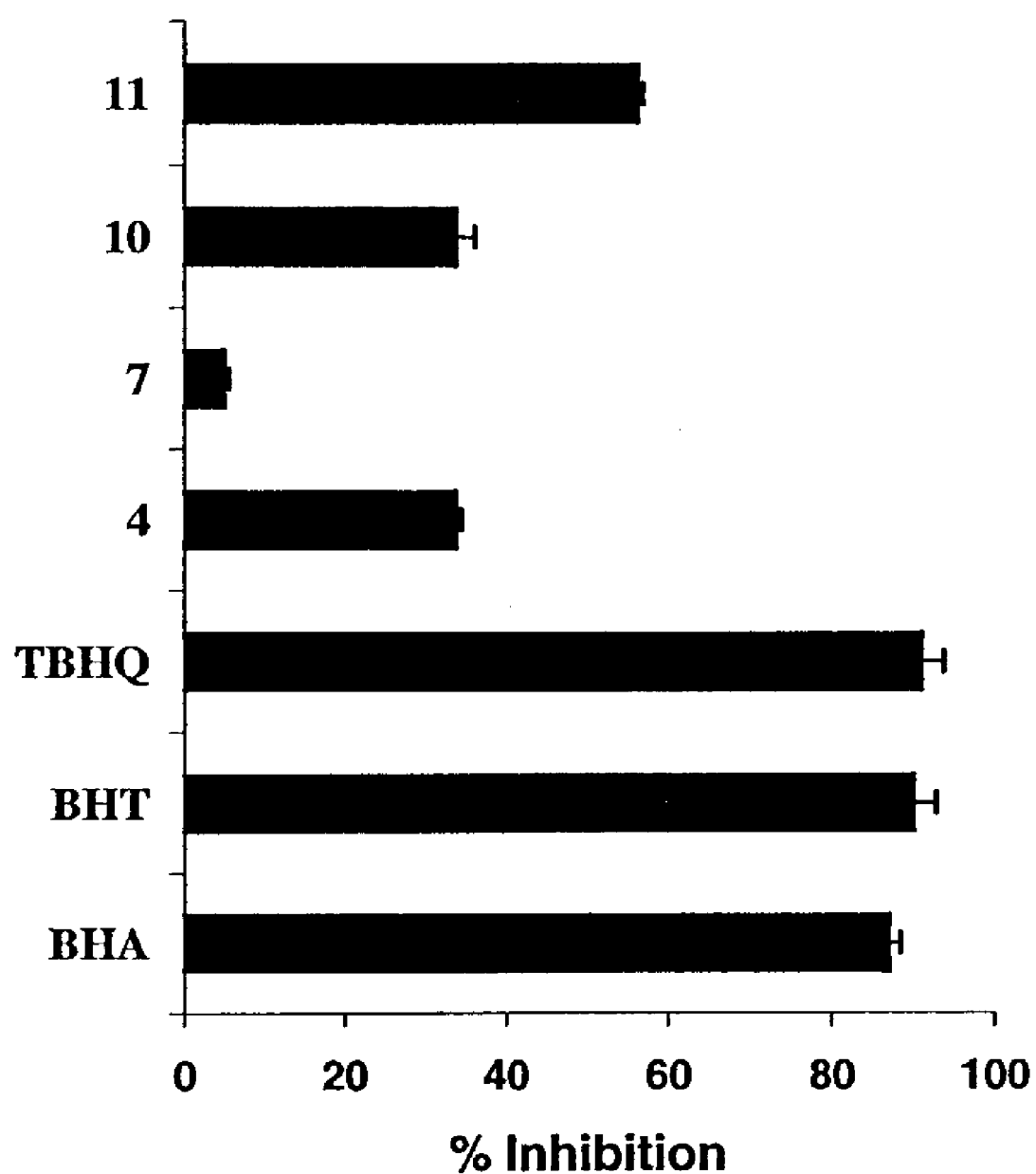
FIG. 5 is a graph showing inhibition of lipid peroxidation at 20 min by compounds 4, 7, 10, and 11 at 100 ppm and synthetic antioxidants BHA, BHT and TBHQ at 10 ppm concentration. DMSO, used as a solvent control, did not show activity. Similarly, withanolides 1–3, 5, 6, 8, 9, and 12 did not show activity at 100 ppm concentration. Data are represented as mean±one standard deviation (n=2).

The ability of withanolides to inhibit lipid peroxidation in a model system was used to determine whether they could act as antioxidants. The assay was conducted by using large unilamellar vesicles and peroxidation was initiated by adding $Fe^{2+}$. Except for compounds 4, 7, 10 and 11, other withanolides tested did not inhibit the lipid peroxidation (FIG. 5). The monoglycosides 4, 7, 10, and 11 inhibited 40, 5, 44 and 55%, respectively, of lipid peroxidation in our assay system.

In vitro results on the COX-2 enzyme inhibitory activities of withanolides provided some scientific support for the use of *W. somnifera* leaf preparation as a folk remedy for the treatment of inflammation (Thakur, R. S., et al., *Major medicinal plants of India;* Ed.; Central Institute of Medicinal and Aromatic Plants: Lucknow, India, p. 531 (1989)). This invention also represents the first report of the COX-2 enzyme inhibitory activity for this group of compounds. Over expression of COX-2 enzyme was observed in tumor cells and hence selective COX-2 inhibitors can prevent tumor progression. Anecdotal reports indicate that the withanolides exhibit anticancer activity (Thakur, R. S., et al., *Major medicinal plants of India;* Ed.; Central Institute of Medicinal and Aromatic Plants: Lucknow, India, p. 531 (1989)). Therefore, these compounds can be useful as templates for the development of therapeutics for cancer chemoprevention. Since both roots and leaves of *W. somnifera* contain similar withanolides, consumption of *W. somnifera* root powder or leaf extract as a dietary supplement can decrease the inflammatory pain, the risk of cancer formation and progression of tumors at levels which suppress the COX-2 enzyme.

Experimental Procedures

General. $^1$H NMR spectra were recorded on a 500 MHz VRX spectrometer. $^{13}$C NMR spectra were obtained at 125 MHz. Chemical shifts were recorded in either CDCl$_3$ or CD$_3$OD. HMBC was optimized for J=8.0 Hz. The silica gel used for MPLC was Merck Silica gel 60 (35–70 μm particle size). HRFAB and FAB mass spectra were acquired on JEOL HX-110 double focusing mass spectrometer operating in the positive mode. Preparative HPLC was performed on a recycling preparative HPLC (Japan Analytical Industry Co. model LC-20) with tandem C$_{18}$ column (JAIGEL, 10 μm, 20×250 mm) at the flow rate of 3 ml/min. All organic solvents and standards used were ACS reagent grade. Yields of the withanolides are expressed in percentage dry weight of the leaves.

Plant Material. The extract (H-341) was purchased from PhytoMyco Research Corporation, Greenville, NC and was prepared as follows: The shade dried and ground leaves of *W. somnifera* were extracted sequentially with a mixture of dichloromethane and methanol (1:1, v/v), methanol and water to obtain three fractions. All fractions were then pooled, filtered and dried under reduced pressure. The resulting extract was stored at −20° C. until use.

Isolation of withanolides. The combined crude extract from PhytoMyco Research Corporation (4 g) was stirred with n-hexane (500 mL) and filtered. The hexane insoluble portion (3.2 g) was chromatographed on MPLC using CHCl$_3$ and MeOH (v/v) under gradient condition. The fractions collected were I (600 mg CHCl$_3$:MeOH, 9:1), II (500 mg, CHCl$_3$:MeOH, 8:2), III (1.2 g, CHCl$_3$:MeOH, 7:3), and IV (200 mg, CHCl$_3$:MeOH, 1:1). Repeated MPLC of fraction I using hexane-EtOAc (1:1, v/v) yielded pure compounds 6 (120 mg, 0.078%), 7 (50 mg, 0.032%) and a fraction 1 (4.0 mg). This fraction was further purified by PTLC (hexane-EtOAc, 6:4, v/v) to yield the pure compound 9 (2.1 mg, 0.0014%). Purification of fraction II by preparative HPLC using MeOH—H$_2$O (1:1, v/v) afforded compound 10 (20 mg, 0.013%) at 19.5 min and fraction 2 (50 mg) at 24.2–28.1 min. It was further purified on HPLC by using MeOH—H$_2$O (4:6, v/v) and gave compound 11 (40 mg, 0.026%) at 32.96 min. Similarly, fraction III was purified by Prep. HPLC (MeOH—H$_2$O, 6:4, v/v) and yield pure compound 12 (15 mg, 0.0097%) at 112 min and fractions 3 (950 mg) at 20–45 min and 4 (16 mg) at 140–160 min. Fraction 3 was further purified by HPLC (MeOH—H$_2$O, 6:4, v/v) to afford compounds 8 (200 mg, 0.13%) and 5 (10 mg, 0.0065%) at 66.8 and 78.6 min, respectively, and 700 mg of sucrose at 132 min. Fraction 4 was subjected to HPLC (MeOH—H$_2$O, 7:3, v/v) yielded compound 2 (12 mg, 0.0078%) at 81 min. The fraction IV was purified by HPLC (MeOH—H$_2$O, 7:3) and collected fractions 5 (13 mg) at 20–30 min and fraction 6 (30 mg) at 30.1–66 min. The fraction 6 was purified by HPLC (MeOH—H$_2$O, 7:3, v/v) to yield compound 3 (8.5 mg, 0.0055%) at 57.9 min. Fraction 5 was further purified by HPLC using MeOH—H$_2$O (6:4, v/v) and afforded pure compound 1 (10.5 mg, 0.0068%) at 59.3 min and a mixture of compounds 4 and 12 at 96.4 min (5.0 mg, 0.0032%).

Compound 1. Colorless, amorphous powder; IR $v_{max}$ (KBr) 3406, 1698, 1650, 1383, 1076, 1042 cm$^{-1}$; $^1$H NMR (CD$_3$OD) δ 0.60 (3H, s, Me-18), 0.90 (3H, s, Me-19), 0.92 (3H, d, J=7.0 Hz, Me-21), 1.90 (3H, s, Me-28), 3.96 (1H, m, H-3), 4.15 (1H, d, J=8.0 Hz, H-1'''), 4.20 (1H, d, J=8.0 Hz, H-1''), 4.22 (1H, d, J=8.0 Hz, H-1'), 4.30 (1H, t, J=2.3 Hz, H-1), 4.35 (2H, br s, H-27), 4.48 (1H, dt, J=13.0, 3.4 Hz, H-22), 5.50 (1H, br. D, J=5.5 Hz, H-6); $^{13}$C NMR data (Table 1); FABMS m/z 945 (M+H$^+$), 783 (M+H$^+$-glucose), 621 (M+H$^+$-2×glucose), 459 (aglycone); HRFABMS m/z 945.4682 (M+H$^+$; calcd for C$_{46}$H$_{73}$O$_{20}$, 945.4695).

TABLE 1

$^{13}$C NMR chemical shifts of withanolides 1–5[a]

| Carbon number | 1 | 2 | 3 | 4 | 5 |
|---|---|---|---|---|---|
| 1 | 74.9 d | 74.9 d | 210.2 s | 75.0 d | 210.6 s |
| 2 | 37.7 t | 37.7 t | 42.6 t | 37.8 t | 52.2 t |
| 3 | 73.6 d | 73.6 d | 70.4 d | 73.6 d | 40.5 t |
| 4 | 39.2 t | 39.1 t | 73.8 d | 75.6 d | 72.8 d |
| 5 | 139.0 s | 139.1 s | 63.8 s | 65.5 s | 64.2 s |
| 6 | 125.5 d | 125.4 d | 56.6 d | 59.4 d | 57.1 d |
| 7 | 30.7 t | 30.8 t | 29.8 t | 30.7 t | 30.0 t |
| 8 | 33.2 d | 33.2 d | 31.0 d | 33.2 d | 31.5 d |
| 9 | 42.7 d | 42.7 d | 42.5 d | 42.7 d | 43.0 d |
| 10 | 42.5 s | 42.6 s | 49.1 s | 53.0 s | 49.5 s |
| 11 | 21.3 t | 21.3 t | 20.7 t | 22.3 t | 21.1 t |
| 12 | 40.4 t | 40.3 t | 27.1 t | 28.2 t | 27.5 t |
| 13 | 43.9 s | 43.9 s | 42.6 s | 44.1 s | 42.9 s |
| 14 | 57.2 d | 57.6 s | 56.1 d | 51.7 d | 55.7 d |
| 15 | 25.5 t | 25.5 t | 24.2 t | 39.2 t | 24.6 t |
| 16 | 28.3 t | 28.3 t | 39.1 t | 79.1 d | 39.4 t |
| 17 | 53.2 d | 53.2 d | 51.8 d | 57.2 d | 50.1 d |
| 18 | 12.1 q | 12.1 q | 10.7 q | 11.9 q | 11.1 q |
| 19 | 20.0 q | 19.9 q | 13.6 q | 15.0 q | 14.0 q |
| 20 | 40.8 d | 40.8 d | 39.0 d | 40.9 d | 39.6 d |
| 21 | 13.7 q | 13.7 q | 12.5 q | 13.6 q | 12.9 q |
| 22 | 80.1 d | 80.2 d | 78.9 d | 80.2 d | 79.4 d |
| 23 | 32.8 t | 32.8 t | 29.6 t | 32.5 t | 30.2 t |
| 24 | 160.4 s | 160.2 s | 159.1 s | 157.8 s | 157.0 s |
| 25 | 123.6 s | 123.6 s | 122.5 s | 125.4 s | 125.6 s |
| 26 | 168.6 s | 168.6 s | 167.4 s | 168.5 s | 167.7 s |
| 27 | 57.6 t | 63.5 t | 61.6 t | 57.6 t | 56.6 t |
| 28 | 20.7 q | 20.7 q | 19.5 q | 20.0 q | 19.5 q |
| 1' | 103.0 d | 102.7 d | 102.7 d | 103.0 d | 72.8 d |
| 2' | 75.1 d | 75.1 d | 75.6 d | 75.6 d | 52.1 s |
| 3' | 78.0 d | 78.1 d | 76.9 d | 78.0 d | 210.1 s |
| 4' | 71.5 d | 71.7 d | 72.4 d | 71.7 d | 25.4 q (4'&5'-Me) |
| 5' | 77.9 d | 78.0 d | 76.8 d | 77.9 d | |
| 6' | 70.0 t | 62.9 t | 62.4 t | 62.7 t | |
| 1'' | 103.9 d | 103.9 d | | | |
| 2'' | 75.0 d | 75.0 d | | | |
| 3'' | 78.0 d | 78.0 d | | | |
| 4'' | 77.8 d | 71.6 d | | | |
| 5'' | 77.9 d | 77.9 d | | | |
| 6'' | 62.7 t | 62.8 t | | | |
| 1''' | 104.8 d | | | | |
| 2''' | 75.0 d | | | | |
| 3''' | 78.0 d | | | | |
| 4''' | 71.5 d | | | | |
| 5''' | 77.9 d | | | | |
| 6''' | 63.5 t | | | | |

[a]Data recorded in CD$_3$OD at 125 MHz at 25° C. Multiplicities were determined by DEPT experiments and confirmed by analysis of HMQC spectra.

Compound 2. Colorless, amorphous powder; IR $v_{max}$ (KBr) 3407, 1696, 1652, 1398, 1040 cm$^{-1}$; $^1$H NMR (CD$_3$OD) δ 0.76 (3H, s, Me-18), 1.01 (3H, s, Me-19), 1.22 (3H, d, J=7.0 Hz, Me-21), 2.11 (3H, s, Me-28), 3.83 (1H, m, H-3), 4.31 (1H, d, J=8.0 Hz, H-1''), 4.36 (1H, d, J=8.0 Hz, H-1'), 4.46 (1H, d, J=11.5 Hz, H-27b), 4.48 (1H, dt, J=13.0, 3.4 Hz, H-22), 4.50 (1H, t, J=2.3 Hz, H-1), 4.60 (1H, d, J=11.5 Hz, H-27a), 5.49 (1H, br. d, J=5.5 Hz, H-6); $^{13}$C NMR data (Table 1); FABMS m/z 783 (M+H)$^+$); HRFABMS m/z 783.4168 (M+H$^+$; calcd. For $C_{40}H_{63}O_{15}$, 783.4188).

Compound 3. Colorless, amorphous powder; IR $v_{max}$ (KBr) 3425, 1700, 1652, 1400, 1259, 1058 cm$^{-1}$; $^1$H NMR (CD$_3$OD) δ 0.67 (3H, s, Me-18), 0.98 (3H, d, J=7.0 Hz, Me-21), 1.18 (3H, s, Me-19), 2.10 (3H, s, Me-28), 3.15 (1H, br s, H-6), 3.33 (1H, d, J=8.0 Hz, H-4), 3.66 (dd, 1H, J=11.0, 3.0 Hz, H-3), 4.31 (1H, d, J=7.5 Hz, H-1'), 4.44 (1H, dt, J=13.5, 3.5 Hz, H-22), 4.45 (1H, d, J=11.5 Hz, H-27b), 4.59 (1H, d, J=11.5 Hz, H-27a); $^{13}$C NMR data (Table 1); FABMS m/z 673 ([M+Na]$^+$). HRFABMS m/z 673.3200 ([M+Na]$^+$; calcd. for $C_{34}H_{50}O_{12}$, 673.3224).

Compound 4. Colorless, amorphous powder; IR $v_{max}$ (KBr) 3424, 1697, 1652, 1398, 1384, 1076, 1042 cm$^{-1}$; $^1$H NMR (CD$_3$OD) δ 0.69 (3H, s, Me-18), 1.0 (3H, d, J=7.0 Hz, Me-21), 1.22 (3H, s, Me-19), 2.08 (3H, s, Me-28), 3.14 (1H, br s, H-6), 3.41 (br t, J=7.5 Hz, H-16), 3.43 (1H, d, J=8.0 Hz, H-4), 3.60 (1H, m, H-3), 4.19 (1H, br s, H-27), 4.38 (1H, d, J=7.5 Hz, H-1'), 4.30 (1H, dt, J=13.5, 3.4 Hz, H-22), 4.46 (1H, t, J=2.3 Hz, H-1); $^{13}$C NMR data (Table 1); FABMS m/z 669 (M+H$^+$), 507 (aglycone); HRFABMS m/z 669.3456 (M+H$^+$; calcd. For $C_{34}H_{53}O_{13}$, 669.3486).

Compound 5. Colorless, amorphous powder; IR $v_{max}$ (KBr) 3434, 1704, 1634, 1397, 1382, 1256, 1236, 1058, 999 cm$^{-1}$; $^1$H NMR (CD$_3$OD) δ 0.69 (3H, s, Me-18), 0.98 (3H, d, J=6.5 Hz, Me-21), 1.18 (3H, s, Me-19), 1.35 (6H, s, Me-4' & 5'), 2.07 (3H, s, Me-28), 3.15 (1H, br s, H-6), 3.19 (1H, t, J=2.3 Hz, H-4), 3.70 (1H, s, Hz, H-1'), 4.28 (1H, d, J=12.0 Hz, H-27), 4.35 (1H, d, J=12.0 Hz, H-27), 4.42 (1H, dt, J=13.0, 3.0 Hz, H-22); $^{13}$C NMR data (Table 1); FABMS m/z 555 (M+H$^+$), 472 [M+H—$C_5H_7O$]$^+$, 471 [M+H—$C_5H_8O$]$^+$; HRFABMS m/z 555.3335 (M+H$^+$; calcd. For $C_{34}H_{50}O_{12}$, 555.3323).

Acid hydrolysis. Compounds 1–5 each 1 mg and 11 (5 mg) were dissolved separately in 6% HCl and heated under reflux for 3 hours. This solution was neutralized with 1N NaOH and extracted with EtOAc. The EtOAc extract was concentrated and the aglycone was characterized by spectral experiments. The aqueous solution was concentrated and analyzed for sugars. It was determined that only D-glucose was present in the aqueous portion.

Compounds 6–12. The structures of compounds 6–12 were derived as withaferin A (6) (Anjaneyulu, A. S. R., et al., Indian J. Chem. Sect. B. 36:161–165 (1997)); 2,3-dihydrowithaferin A (7) (Anjaneyulu, A. S. R., et al., Indian J. Chem. Sect. B. 36:161–165 (1997)); viscalactone B (8) (Pelletier, S. W., et al., Heterocycles 15:317–320 (1981)); 23,24-dihydrowithaferin A (9) (Kirson, I., et al., Tetrahedron 26:2209–2219 (1970)); sitoindoside IX (10) (Ghosal, B., et al., Ind. J. Nat. Prod. 4:12–13 (1988)); physagulin D (11) (Shingu, K., et al., Chem. Pharm. Bull. 40:2088–2091 (1992)); and withanolide IV (12) (Matsuda, M., et al., Bioorg. Med. Chem. 9:1499–1507 and references cited therein (2001)) by detailed $^1$H and $^{13}$C NMR spectral experiments. The spectral data of these compounds were identical to their respective published spectral data.

CD analysis. CD spectra for compounds 1–5 were recorded on a JASCO, model J-710, CD-ORD spectrometer in MeOH under the following conditions: scan mode (wave length), band width (0.5 nm), sensitivity (50 m deg), response (1 sec), wave length range (200–400 nm), step resolution (1 nm), scan speed (100 nm min$^{-1}$), and accumulation (1). The CD maximum or minimum (Δε) observed for compounds 1–5 were: 1 (c 0.001, MeOH) Δε +73.7 (257); 2 (c 0.0005, MeOH) Δε +15.4 (262.5); 3 (c 0.001, MeOH) Δε +4.7 (261); 4 (c 0.0005, MeOH) Δε +61.6 (260) and 5 (c 0.001, MeOH) Δε +9.8 (260).

EXAMPLE 13

Cyclooxygenase enzyme inhibitory assay. COX-1 enzyme was prepared from ram seminal vesicles and COX-2 enzyme was isolated from insect cells cloned with human PGHS-2 enzyme. The inhibitory effects of test compounds on COX-1 and -2 were measured by monitoring the initial rate Of $O_2$ uptake using an oxygen electrode (Instech Laboratories, Plymouth Meeting, Pa.) attached to a biological oxygen monitor (Yellow Spring Instrument, Inc., Yellow Spring, Ohio) at 37° C. The enzymes were diluted (1:1) with Tris buffer (pH 7, 10–15 μl) and the test compounds (100 μg/ml, 10 μl) dissolved in DMSO were added to the assay mixture composed of 3 ml of 0.1 M Tris HCl, pH 7, 1 mmol phenol and 85 μg of hemoglobin. The mixture was incubated for 2–3 min and reaction was initiated by the addition of arachidonic acid (10 μl of 1.64 μM solution). The instantaneous inhibition was measured by using Quick Log Data acquisition and control computer software (Strawberry Tree Inc., Sunnyvale, Calif., USA). Positive controls aspirin, ibuprofen, naproxen were tested at 180, 2.1 and 2.5 μg/ml, respectively, and Celebrex, Vioxx and Bextra were tested at 1.67 μg/ml. DMSO was used as solvent control (Wang, H., et al., J. Nat. Prod. 62:294–296 (1999)). The results are shown in FIGS. 3A and 3B. FIG. 4 shows the results with withanolides 1 to 5.

EXAMPLE 14

Antioxidant activity. Large Unilamellar Vesicles (Liposome suspension) were prepared according to the published procedure (Ramsewak, R. S., et al., Phytomedicine 7:303–308 (2000). The final assay volume was 2 ml, consisting of 100 μl HEPES buffer (50 mM HEPES and 50 mM TRIS), 200 μl 1M NaCl, 1.64 ml of $N_2$-sparged water, 20 μl of test sample or DMSO and 20 μl of liposome suspension. The peroxidation was initiated by the addition of 20 μl of $FeCl_2.4H_2O$ (0.5 mM). The fluorescence was monitored at 0, 1, 3 and every 3 min up to 21 min using a Turner Model 450 Digital Fluorometer. The decrease of relative fluorescence intensity over the time indicated the rate of peroxidation. The percentage of inhibition was calculated with respect to DMSO control. All compounds were tested at 100 μg/ml and the positive controls BHA, BHT and TBHQ were tested at 10 μM. The results are shown in FIG. 5.

Pharmaceutical Compositions

In pharmaceutical compositions, the withanolide is inhibitory at a dosage of 1 to 1,000 micrograms per milliliter or gram. In a preferred embodiment, one or more of the withanolides for treating a patient are provided to the patient at an inhibitory dose in a pharmaceutically acceptable carrier. As such, the withanolides are processed with pharmaceutical carrier substances by methods well known in the art such as by means of conventional mixing, granulating, coating, suspending and encapsulating methods, into the customary preparations for oral or rectal administration. Thus, withanolide preparations for oral application can be obtained by combining one or more of the anthraquinones with solid pharmaceutical carriers; optionally granulating the resulting mixture; and processing the mixture or granulate, if desired and/or optionally after the addition of suitable auxiliaries, into the form of tablets or dragee cores.

Suitable pharmaceutical carriers for solid preparations are, in particular, fillers such as sugar, for example, lactose, saccharose, mannitol or sorbitol, cellulose preparations and/or calcium phosphates, for example, tricalcium phosphate or calcium hydrogen phosphate; also binding agents, such as starch paste, with the use, for example, of maize, wheat, rice or potato starch, gelatine, tragacanth, methyl cellulose, hydroxypropylmethyl cellulose, sodium carboxymethyl cellulose and/or polyvinylpyrrolidone, esters of polyacrylates or polymethacrylates with partially free functional groups; and/or, if required, effervescent agents, such as the above-mentioned starches, also carboxymethyl starch, cross-linked polyvinylpyrrolidone, agar, or alginic acid or a salt thereof, such as sodium alginate. Auxiliaries are primarily flow-regulating agents and lubricating agents, for example, silicic acid, talcum, stearic acid or salts thereof, such as magnesium stearate or calcium stearate. Dragee cores are provided with suitable coatings, optionally resistant to gastric juices, whereby there are used, inter alia, concentrated sugar solutions optionally containing gum arabic, talcum, polyvinylpyrrolidone, and/or titanium dioxide, lacquer solutions in aqueous solvents or, for producing coatings resistant to stomach juices, solutions of esters of polyacrylates or polymethacrylates having partially free functional groups, or of suitable cellulose preparations such as acetylcellulose phthalate or hydroxypropyl-methylcellulose phthalate, with or without suitable softeners such as phthalic acid ester or triacetin. Dyestuffs or pigments may be added to the tablets or dragee coatings, for example for identification or marking of the various doses of active ingredient.

Withanolide preparations comprising one or more of the anthraquinones which can be administered orally further include hard gelatine capsules, as well as hard or soft closed capsules made from gelatine and, if required, a softener such as glycerin or sorbitol. The hard gelatine capsules can contain one or more of the withanolides in the form of a granulate, for example in admixture with fillers such as maize starch, optionally granulated wheat starch, binders or lubricants such as talcum, magnesium stearate or colloidal silicic acid, and optionally stabilizers. In closed capsules, the one or more of the withanolides is in the form of a powder or granulate; or it is preferably present in the form of a suspension in suitable solvent, whereby for stabilizing the suspensions there can be added, for example, glycerin monostearate.

Other withanolide preparations to be administered orally are, for example, aqueous suspensions prepared in the usual manner, which suspensions contain the one or more of the anthraquinones in the suspended form and at a concentration rendering a single dose sufficient. The aqueous suspensions either contain at most small amounts of stabilizers and/or flavoring substances, for example, sweetening agents such as saccharin-sodium, or as syrups contain a certain amount of sugar and/or sorbitol or similar substances. Also suitable are, for example, concentrates or concentrated suspensions for the preparation of shakes. Such concentrates can also be packed in single-dose amounts.

Suitable withanolide preparations for rectal administration are, for example, suppositories consisting of a mixture of one or more of the withanolides with a suppository foundation substance. Such substances are, in particular, natural or synthetic triglyceride mixtures. Also suitable are gelatine rectal capsules consisting of a suspension of the one or more of the withanolides in a foundation substance. Suitable foundation substances are, for example, liquid triglycerides, of higher or, in particular, medium saturated fatty acids.

Likewise of particular interest are preparations containing the finely ground one or more of the withanolides, preferably that having a median of particle size of 5 µm or less, in admixture with a starch, especially with maize starch or wheat starch, also, for example, with potato starch or rice starch. They are produced preferably by means of a brief mixing in a high-speed mixer having a propeller-like, sharp-edged stirring device, for example with a mixing time of between 3 and 10 minutes, and in the case of larger amounts of constituents with cooling if necessary. In this mixing process, the particles of the one or more of the withanolides are uniformly deposited, with a continuing reduction of the size of some particles, onto the starch particles. The mixtures mentioned can be processed with the customary, for example, the aforementioned, auxiliaries into the form of solid dosage units; i.e., pressed for example into the form of tablets or dragees or filled into capsules. They can however also be used directly, or after the addition of auxiliaries, for example, pharmaceutically acceptable wetting agents and distributing agents, such as esters of polyoxyethylene sorbitans with higher fatty acids or sodium lauryl sulphate, and/or flavoring substances, as concentrates for the preparation of aqueous suspensions, for example, with about 5- to 20-fold amount of water. Instead of combining the withanolide/starch mixture with a surface-active substance or with other auxiliaries, these substances may also be added to the water used to prepare the suspension. The concentrates for producing suspensions, consisting of the one or more of the withanolide/starch mixtures and optionally auxiliaries, can be packed in single-dose amounts, if required in an airtight and moisture-proof manner.

In addition, the one or more withanolides can be administered to a patient intraperitoneally, intranasally, subcutaneously, or intravenously. In general, for intraperitoneal, intranasal, subcutaneous, or intravenous administration, one or more of the withanolides are provided by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the one or more withanolides are provided in a composition acceptable for intraperitoneal, subcutaneous, or intravenous use in warm-blooded animals or humans. For example, such compositions can comprise a physiologically acceptable solution such as a buffered phosphate salt solution as a carrier for the one or more anthraquinones. Preferably, the solution is at a physiological pH. In particular embodiments, the composition is injected directly into the patient perfused through the tumor by intravenous administration.

Preparations according to the present invention comprise one or more of the withanolides at a concentration suitable for administration to warm-blooded animals or humans which concentration is, depending on the mode of administration, between about 0.3% and 95%, preferably between about 2.5% and 90%. In the case of suspensions, the concentration is usually not higher than 30%, preferably about 2.5%; and conversely in the case of tablets, dragees and capsules with the one or more of the anthraquinones, the concentration is preferably not lower than about 0.3%, in order to ensure an easy ingestion of the required doses of the one or more withanolides. The treatment of patients with the preparations comprising one or more of the withanolides is carried out preferably by one or more administrations of a dose of the one or more withanolide which over time is sufficient to substantially inhibit COX-2. If required, the doses can be administered daily or divided into several partial doses which are administered at intervals of several hours. In particular cases, the preparations can be used in conjunction with or following one or more other therapies such as radiation or chemotherapy. The administered dose of the one or more withanolides is dependent both on the patient (species of warm-blooded animal or human) to be treated, the general condition of the patient to be treated, and on the type of disease to be treated.

It is intended that the foregoing description be only illustrative of the present invention and that the present invention be limited only by the hereinafter appended claims.

We claim:

1. A method for selectively inhibiting COX2 enzyme relative to COX1 enzyme in a patient in need thereof which comprises administering to the patient in need thereof an effective amount of at least one isolated and purified withanolide selected from the group consisting of physagulin D (1→6)-β-D-glucopyranosyl-(1→4)-β-D-glucopyranoside; 27-O-β-D-glucopyranosyl physagulin D; 27-O-β-D-glucopyranosyl viscosalactone B; 4,16-dihydroxy-5β,6β-epoxyphysagulin D; and, 4-(1-hydroxy-2,2-dimethylcyclo-propanone)-2, and 3-dihydrowithaferin A so as to produce the COX2 inhibition in the patient in need thereof.

2. A method for selectively inhibiting COX2 enzyme relative to COX1 enzyme in a patient in need thereof which comprises administering an effective amount of at least one isolated and purified withanolide selected from the group consisting of physagulin D (1→6)-β-D-glucopyranosyl-(1→4)-β-D-glucopyranoside; 27-O-β-D-glucopyranosyl physagulin D; 27-O-β-D-glucopyranosyl viscosalactone B; 4,16-dihydroxy-5β,6β-epoxyphysagulin D; and, 4-(1-hydroxy-2,2-dimethylcyclo-propanone)-2, and 3-dihydrowithaferin A in a pharmaceutically acceptable carrier in vivo to a patient in need thereof so as to produce the COX2 inhibition.

3. The method of claim 1 or 2 wherein the inhibition is in vivo in a mammal.

4. A method for selectively inhibiting COX2 enzyme relative to COX1 enzyme in a patient in need thereof which comprises administering to said patient in need thereof, an effective amount of an isolated and purified compound selected from the group consisting of physagulin D (1→6)-β-D-glucopyranosyl-(1→4)-β-D-glucopyranoside; 27-O-β-D-glucopyranosyl physagulin D; 27-O-β-D-glucopyranosyl viscosalactone B; 4,16-dihydroxy-5β,6β-epoxyphysagulin D; 4-(1-hydroxy-2,2-dimethylcyclo-propanone)-2, 3-dihydrowithaferin A; and, mixtures thereof and a compound selected from the group consisting of 2,3-dihydrowithaferin A; viscosalactone B; 23,24-dihydrowithaferin A; sitoindoside IX; physagulin D; withanoside IV; and, mixtures thereof to said patient so as to produce the COX2 inhibition in the patient.

* * * * *